(12) United States Patent
Wang et al.

(10) Patent No.: US 9,417,206 B2
(45) Date of Patent: Aug. 16, 2016

(54) APPARATUS FOR RESIDUAL PESTICIDE DETECTION

(71) Applicant: BRILLIANT SENSING TECHNOLOGY, New Taipei (TW)

(72) Inventors: Wen Wang, New Taipei (TW);
Kuan-Jung Chen, New Taipei (TW);
Kuan-Yu Chen, New Taipei (TW);
Shin-Pang Yang, New Taipei (TW)

(73) Assignee: BRILLIANT SENSING TECHNOLOGY, New Taipei (TW)

( * ) Notice: Subject to any disclaimer, the term of this patent is extended or adjusted under 35 U.S.C. 154(b) by 153 days.

(21) Appl. No.: 14/523,649

(22) Filed: Oct. 24, 2014

(65) Prior Publication Data
US 2015/0300976 A1 Oct. 22, 2015

(30) Foreign Application Priority Data

Dec. 23, 2013 (TW) .............................. 102224216 U

(51) Int. Cl.
G01N 27/327 (2006.01)
G01N 33/18 (2006.01)

(52) U.S. Cl.
CPC ...... *G01N 27/3272* (2013.01); *G01N 2033/184* (2013.01)

(58) Field of Classification Search
CPC ............ G01N 27/327; G01N 27/3272; G01N 2033/184
See application file for complete search history.

(56) References Cited

U.S. PATENT DOCUMENTS

| 2003/0024811 | A1* | 2/2003 | Davies | ................... | C12Q 1/002 204/403.01 |
| 2005/0100880 | A1* | 5/2005 | Chang | ................ | G01N 33/5438 435/4 |
| 2005/0247573 | A1* | 11/2005 | Nakamura | ......... | G01N 27/3272 205/777.5 |

* cited by examiner

Primary Examiner — Bryan D. Ripa
(74) Attorney, Agent, or Firm — Maschoff Brennan

(57) ABSTRACT

Disclosed is an apparatus for pesticide detection in aqueous solution was provided, wherein an electrochemical biosensor, a container for mixing and an electrical signal analyzer were used, and the biosensor is disposable.

10 Claims, 4 Drawing Sheets

APPARATUS FOR RESIDUAL PESTICIDE DETECTION

FIELD OF THE INVENTION

The present invention relates to an apparatus for detecting concentration of pesticide residues in aqueous solution, and more particularly to an electrochemical biosensor for quantifying concentration of pesticide residues.

BACKGROUND OF THE INVENTION

For increasing crop production and better appearance of crops, farmers usually spray a great deal of pesticide on crops to protect them from attacks by insect pests. Currently, organophosphate pesticides and carbamate pesticides have replaced organochlorine pesticides, thereby becoming the most widely used pesticides as a consequence of low bioaccumulation and high biodegradability. In spite of the advantages mentioned above, organophosphate pesticides and carbamate pesticides still result in residues building up in the soil, crops, surface water and industrial wastewater, causing considerable threats to human health and the natural environment in the case of heavy use. Particularly, both of the above-mentioned pesticides are neurotoxins. Once one of them enters into an organism, it will inhibit activity of acetylcholine esterase by irreversibly binding to the active site thereof so as to slow down hydrolysis rate of acetylcholine and interfere neural transmission. Depending on the toxicity, dosage and duration of contact of the pesticide itself, such pesticides have resulted in different symptoms such as fatigue, nausea, sleepiness, blurry vision and even death. Thus, countries around the world have paid close attention to control such nerve inhibiting pesticides. Fairly strict regulatory standards, especially on pesticide involved in drinking water, food and industrial wastewater, have been imposed.

The conventional methods of pesticide residue analysis, especially for pesticide residues in vegetables and fruits, include spectrophotometry, nuclear magnetic resonance spectroscopy, thin layer chromatography, atomic absorption spectroscopy, gas chromatograpy, liquid chromatography, fluorimetry and so on, among which gas chromatograpy and liquid chromatography are more commonly used due to advantages of favorable repeatability, sensitivity, and capability of determining pesticide type and concentration. However, such methods have to be executed by following standard detection steps as well as by laboratory technicians equipped with the expertise conducting sample pretreatment and performing analysis via instrumental operation in order to obtain valid detection results. Thus, conventional detection of pesticide residues can not be applied to a large quantity of agricultural products rapidly and conveniently. In recent years, several methods for detecting enzyme inhibiting pesticides by means of biochemical reaction and electrochemistry technique have been developed. For example, U.S. Pat. No. 6,406, 876 (Gordon et al.) has disclosed an immobilized enzyme technology without making a huge amount of solution. However, drawbacks of immobilized enzyme include high cost, complicated manufacturing process and stringent preservation conditions. Thus, analysis should be performed by professionals. Both TW patent M376764 and CN patent CN101082599 (Lin et al.) have disclosed a simpler and more convenient method of immobilizing enzyme on the analytical apparatus to detect pesticide residue concentration. However, the design approach is more complicated in which enzyme and related reactant have to be stored respectively in the electrodes and sample containers so that two-phase reactions are proceeded respectively, likely to result analysis errors. Besides, TW patent 1301541 (Wu et al.) has disclosed a method for immobilizing enzyme on the electrode to determine pesticide concentration in aqueous solution via the degree of enzyme inhibition caused by pesticides. However, the method of immobilizing enzyme is more complicated. Mass production is difficult. Moreover, the quantitative method of pesticide residue concentration is simply presented by the rate of enzyme inhibition, thereby making a user who operates the apparatus unable to figure out clearly the actual amount of pesticide residue.

In view of the above reasons, it is necessary to propose a simple and innovative analytical apparatus devised to minimize the measurement errors in concentration of pesticide residues in a more simple design approach. Moreover, a user who is not equipped with the expertise can detect pesticide residue concentration in a rapid and convenient manner and immediately gain a practical understanding of the amount of pesticide residue.

SUMMARY OF THE INVENTION

The present invention is to provide a rapid and stable apparatus for quantifying concentration of pesticide residues in aqueous solution utilizing inhibition of acetylcholinesterase activity by organophosphate pesticides and carbamate pesticides.

The present invention is to provide an apparatus for residual pesticide detection that includes a disposable electrode strip body having an insulating substrate, the disposable electrode strip body being divided into a first strip portion and a second strip portion, the first strip portion being with an electrode pattern placed on the insulating substrate, the second strip portion being without an electrode pattern placed on the insulating substrate, a splitting line being located between the first strip portion and the second strip portion and being between the insulating substrate, the splitting line being split to separate the first strip portion and the second strip portion from each other and separate the insulating substrate apart, wherein the first strip portion is provided with a working electrode area for depositing a predetermined amount of a first reactant (enzymatic mixture layer) thereon, and the second strip portion is for depositing a predetermined amount of a second reactant (reactant layer) thereon; a mixing container for containing a predetermined volume of sample liquid to be tested and for containing the second strip portion, wherein the second reactant of the second strip portion is dissolved absolutely in the liquid sample to form mixed aqueous solution; an electrical signal analyzer, connected to the first strip portion, for detecting an electrical current signal to obtain normality of pesticide residue in the sample liquid as compared to a predetermined pesticide, wherein the electrical current signal is detected by introducing the mixed aqueous solution into the working electrode area via a micro-channel of the first strip portion to react with the first reactant for a time period, and applying a voltage to the first strip portion.

Another object of the present invention is to provide instruction and presentation of the apparatus for residual pesticide detection that include following steps: (a) Prepare sample liquids to be tested containing known pesticides with different concentrations for acting as standard substances. Detect the sample liquids to be tested containing known pesticides with different concentrations by use of the apparatus for pesticide residue detection mentioned above to obtain its electrical current signal; (b) plot a calibration curve according to each different pesticide concentration and intensity of its corresponding electrical current signal; (c) detect sample liquid to be tested containing unknown pesticide and concentration by use of the apparatus for pesticide residue detection to obtain its electrical current signal; (d) an intensity value of the electrical current signal obtained in the step (c) can be converted into normality corresponding to the standard substance by use of the calibration curve generated in the step (b). The calculation and the presentation mentioned above are according to inhibition of working on acetylcholinesterase by a specific pesticide that can be converted into electrical current signal to generate the calibration curve so as to further calculate normality of any type of pesticide with capability of inhibiting acetylcholinesterase.

In the present invention, a predetermined volume of an enzymatic mixture and a predetermined volume of reactant are provided in aqueous solution containing pesticide in which the catalytic reaction and conversion of the reactant occur. The present invention is achieved based on a fact that the catalytic capability of the enzymatic mixture can be inhibited by the pesticide, and it will reduces the extent of conversion of the reactant. Thus, the amount of pesticide in aqueous solution can be calculated through the variation of reactant conversion. In the present invention, the reactant of the second reaction is converted into the product of the second reaction such as hydrogen peroxide under catalyzing condition by specific chemical substance of the enzymatic mixture, such as choline oxidase. Intensity of an electric current signal obtained through the hydrogen peroxide participating in electrochemical reaction can be further converted into concentration of pesticide in aqueous solution.

The application of enzymatic mixture in the present invention is mainly to change the collocation of two types of enzyme for proceeding series reaction from conventional two-phase reaction occurring in the two reaction areas to single-phase reaction occurring in the single reaction area. Specifically, there is a series-parallel continuous reaction in the present invention. Acetylcholine competes with pesticide for acetylcholinesterase in the single reaction area at the same time to form two-phase succession. The single-phase sequential reaction is more effective for detecting an extremely low concentration of pesticide residues so as to increase sensitivity and limit of pesticide detection as compared to the conventional two-phase inhibition and catalytic reaction of acetylcholinesterase or single-phase inhibition and electronic media reaction of acetylcholinesterase.

Besides, in the present invention, all the enzyme and the reactant have been disposed and preserved on the disposable electrode strip body before proceeding detection of sample liquid to be tested to dispense with the procedure of dispensing or preprocessing. In addition, the apparatus for pesticide residue detection of the present invention can also act as reference for rapid screening for whether excessive presence of pesticide residues is found in the crops.

DETAILED DESCRIPTION OF THE PREFERRED EMBODIMENTS

The structure and the technical means adopted by the present invention to achieve the above and other objects can be best understood by referring to the following detailed descriptions of the preferred embodiments and the accompanied drawings.

The descriptions herein should not be taken as limiting the present invention but only for illustrating the present invention.

Figure 3:
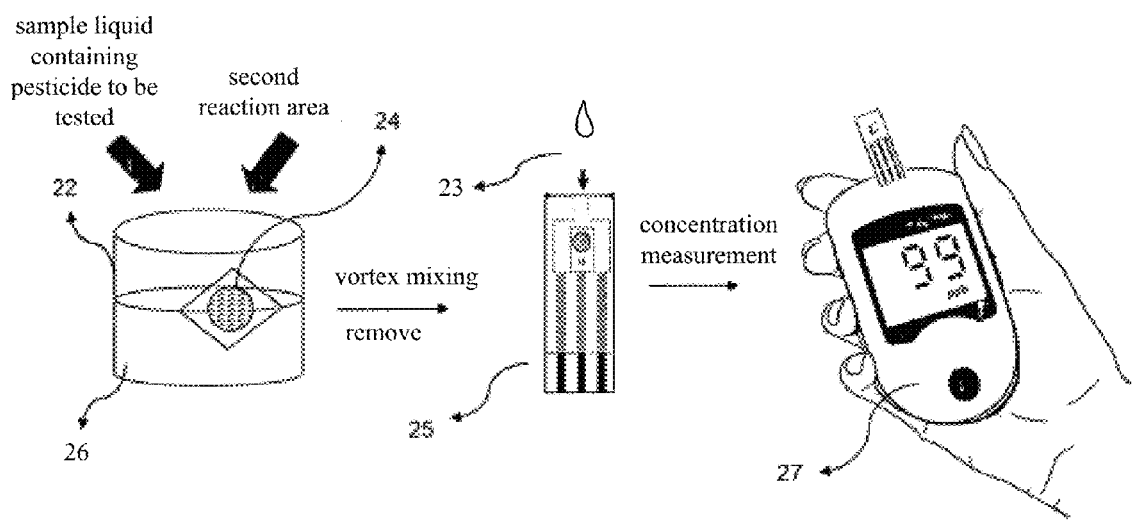
FIG. 3 is operational processes of an apparatus for residual pesticide detection of the present invention.

An apparatus for residual pesticide detection according to the present invention includes a disposable electrode strip body, a mixing container 22 and an electrical signal analyzer 27. The disposable electrode strip body is divided into a first strip portion and a second strip portion, wherein the first strip portion is provided with a first reaction area 25 and the second strip portion is provided with a second reaction area 24. A splitting line 20 is located between the first strip portion and the second strip portion, and the splitting line is split to separate the first strip portion and the second strip portion from each other. A sample liquid to be tested 26 containing pesticide is prepared before quantifying and then is mixed with reactant in the mixing container 22 for subsequent detection and analysis. As shown in FIG. 3, the electrical signal analyzer 27 is connected with the first reaction area 25 for detecting and analyzing the amount of pesticide in the sample liquid to be tested 26 which is converted into normality. Types of pesticides to be tested which are capable of inhibiting activity of enzyme with capability of catalyzing neurotransmitter, i.e., butyrylcholinesterase(BchE) and acetylcholinesterase(AChE), include organophosphate pesticides, carbamate pesticides, neonicotinoid pesticides, etc.

Figure 1:
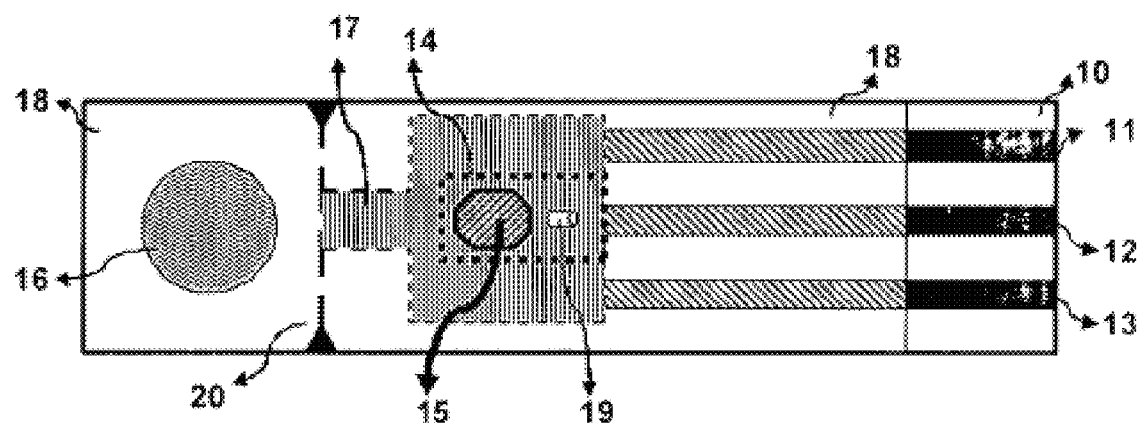
FIG. 1 is a schematic view of a disposable electrode strip body of the present invention.

As shown in FIG. 1, the chemical ingredients included in the present invention are mainly deposited on the disposable electrode strip body.

The first reactant 15 is an enzymatic mixture composed of acetylcholinesterase(AchE) for catalyzing acetylcholine (Ach), and cholineoxidase($ChO_x$) for oxidizing choline.

The second reactant 16 includes composition of Ach with capability of hydrolysis.

The chemical reactions related to the present invention are as follows:

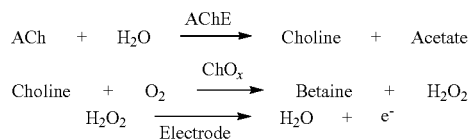

It can be seen according to the above chemical equations when aqueous solution formed by ACh of the second reactant 16 dissolved in the water is applied to an area containing the first reactant 15, ACh is hydrolyzed to choline and acetate catalyzed by AChE, and products of betaine and $H_2O_2$ are produced by the further oxidation of choline catalyzed by $ChO_x$. Furthermore, an electrical current signal is generated when a voltage is applied to the area containing the first reactant 15 and the product of $H_2O_2$ is accumulated thereon, and at the same time $H_2O_2$ decomposes to $H_2O$. After that, a standard value corresponding to a formation rate of choline can be obtained according to the electrical current signal.

According to the sequence of the chemical equations and generation principles of each product as mentioned above, it can be understood when the sample liquid to be tested 26 containing pesticide with capability of inhibiting AChE is detected, the formation rate of choline declines even lower than said standard value since part of activity of AChE has been inhibited by pesticide under constant concentration of Ach. Therefore, the concentration of the residual pesticide in the sample liquid to be tested 26 can be deduced by comparing with the variation of formation rate of choline, i.e., the variation of electric current of the final electrochemical reaction. Besides, in the present invention, only activity of AchE would be inhibited by pesticide while activity of $ChO_x$ is unaffected.

Figure 2:
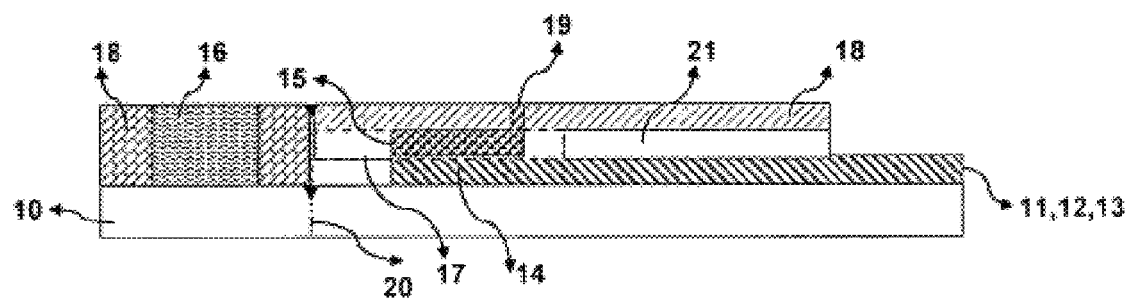
FIG. 2 is an explosion diagram of the disposable electrode strip body according to the present invention.

The following are descriptions of the apparatus and the embodiment in the present invention according to the reaction principle mentioned above. FIG. 1 is a schematic view of the disposable electrode strip body according to an embodiment of the present invention, and FIG. 2 is an explosion diagram of the disposable electrode strip body according to the present invention. The disposable electrode strip body is with an insulating substrate 10, and the disposable electrode strip body is divided into a first strip portion and a second strip portion, wherein the first strip portion is with an electrode pattern placed on the insulating substrate 10, the second strip portion is without an electrode pattern placed on the insulating substrate 10. The splitting line 20 is located between the first strip portion and the second strip portion and is within an intersection of the insulating substrate 10. The splitting line 20 is split to separate the first strip portion and the second strip portion from each other and to separate the insulating substrate 10 apart, wherein the first strip portion is provided with a working electrode area 14 for depositing a predetermined amount of the first reactant 15 thereon, and the second strip portion is for depositing a predetermined amount of the second reactant 16 thereon. The insulating substrate 10 is provided with circuit pattern of a reference electrode 11, a working electrode 12 and an auxiliary electrode 13 by means of printing or deposition. The insulating substrate 10 is covered partially by an insulating layer 21 that defines the working electrode area 14 in which electrochemical reaction occurs and a side wall of a micro-channel 17 for introducing the sample liquid to be tested 26 into the working electrode area 14. The insulating layer 21 is attached closely by a cover layer 18 with a partial gas vent 19. The cover layer 18 is for covering the micro-channel 17, and the gas vent 19 is arranged over the working electrode area 14. The splitting line 20 is formed by a cutting tool or laser.

As shown in FIG. 3, a predetermined volume of sample liquid to be tested 26 containing pesticide is disposed in the mixing container 22, and the second strip portion containing the second reaction area 24 is thrown into the mixing container 22 as well, wherein the second reactant 16 is dissolved absolutely in the sample liquid to be tested 26 by mechanical force to form a mixed aqueous solution 23. Then, the predetermined volume of the mixed aqueous solution 23 containing the second reactant, Ach, and sample liquid to be tested 26 is introduced into the working electrode area 14 via the micro-channel 17 for 3 to 10 minutes, and an electrode connector of the first strip portion is inserted into a connector of the electrical signal analyzer 27 in which voltage is applied to obtain the electric current signal under specific reaction time.

The following are steps of calculation and presentation of residual pesticide according to the apparatus and the embodiment mentioned above of the present invention.

A step of preparing a sample liquid to be tested 26 containing known pesticide type and concentration, in which carbofuran is taken for example in the present invention. Disposing 10 ml of the sample liquid to be tested 26 containing carbofuran in the mixing container 22.

A step of getting the disposable electrode strip body and breaking it along the splitting line 20. Throwing the second strip portion into the mixing container 22 and making the second reactant 16 dissolved absolutely in the sample liquid to be tested 26 containing carbofuran to form the mixed aqueous solution 23 by vortex.

Figure 4:
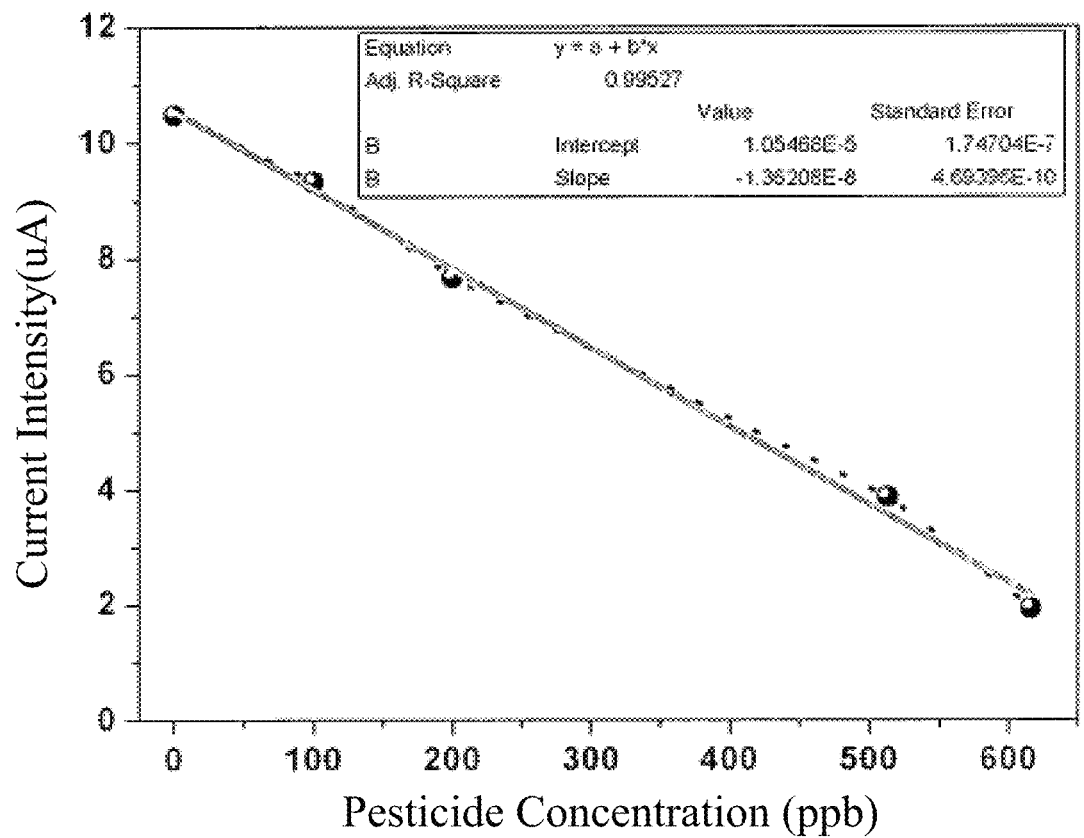
FIG. 4 is a calibration diagram between each different pesticide residue concentration and intensity of its corresponding electrical current signal of the present invention.

A step of taking the electrical signal analyzer 27 to detect the mixed aqueous solution 23 to obtain its corresponding electrical current signal. Plotting a graph by electrical current versus carbofuran concentration to obtain a calibration curve between each different carbofuran concentration and intensity of its corresponding generated electrical current signal as shown in FIG. 4. It is found that there is a linear relationship between carbofuran concentration and its corresponding generated electrical current signal, that is, y=ax+b, wherein y is electrical current signal degree; x is carbofuran concentration; a is slope; b is intercept.

Afterwards, a step of taking target of sample liquid to be tested 26 containing unknown pesticide type and concentration into the mixing container 22 in which the second strip portion is thrown as well, and making the second reactant 16 dissolved absolutely in the sample liquid to be tested 26 to form another mixed aqueous solution 23 by vortex. Introducing predetermined volume of mixed aqueous solution 23 into the working electrode area 14 via the micro-channel 17 of the first strip portion to contact with the first reactant 15 so as to proceed activity-inhibited reaction of AChE and catalyzed reaction of $ChO_x$ at the same time.

Finally, a step of applying specific voltage from the electrical signal analyzer 27 to the working electrode area 14 through the electrode on the disposable electrode strip body to make hydrogen peroxide generated from oxidation reaction of $ChO_x$ decomposed and converted into electrical current signal with a specific intensity.

A step of substituting the electrical current signal of the sample liquid to be tested 26 containing unknown pesticide amount and concentration into the equation mentioned above "y=ax+b" to obtain normality of the sample liquid to be tested 26 containing unknown pesticide amount and concentration corresponding to carbofuran concentration, wherein x is the normality.

Incidentally, the equation "y=ax+b" can be converted as following for calculating conveniently:

$$"x = \frac{y-b}{a}"$$

It is noted that the normality is not the actual pesticide concentration but is the degree corresponding to activity of AChE inhibited by carbofuran under the same dosage of AChE. Thus, no matter how many types of pesticides capable of inhibiting activity of AChE contained in the sample liquid to be tested 26, the concentration of pesticide residues in the sample liquid can be known by the combination of the apparatus for pesticide residue detection and the equation of the present invention.

The above description should be considered as only the discussion of the preferred embodiments of the present invention. However, a person with an ordinary skill in the art may make various modifications to the present invention. Those modifications still fall within the spirit and scope defined by the appended claims.

What is claimed is:
1. An apparatus for residual pesticide detection, comprising:
   a disposable electrode strip body having an insulating substrate, the disposable electrode strip body being divided into a first strip portion and a second strip portion, the first strip portion being with an electrode pattern placed on the insulating substrate, the second strip portion being without an electrode pattern placed on the insulating substrate, a splitting line being located between the first strip portion and the second strip portion and being between the insulating substrate, the splitting line being split to separate the first strip portion and the second strip portion from each other and separate the insulating substrate apart, wherein the first strip portion is provided with a working electrode area having a predetermined amount of a first reactant thereon, and the second strip portion having a predetermined amount of a second reactant thereon;

a mixing container for containing a predetermined volume of sample liquid to be tested and for containing the second strip portion, wherein the second reactant of the second strip portion is dissolved absolutely in the sample liquid to form mixed aqueous solution; and an electrical signal analyzer, connected to the first strip portion, for detecting an electrical current signal to obtain normality of pesticide residue in the sample liquid as compared to a predetermined pesticide, wherein the electrical current signal is detected by:

introducing the mixed aqueous solution into the working electrode area via a micro-channel of the first strip portion to react with the first reactant for a time period, and applying a voltage to the first strip portion.

2. The apparatus for residual pesticide detection as claimed in claim 1, wherein the first reactant is an enzymatic mixture composed of acetylcholinesterase and cholineoxidase or the first reactant is an enzymatic mixture composed of butyrylcholinesterase and cholineoxidase, and the second reactant is acetylcholine.

3. The apparatus for residual pesticide detection as claimed in claim 1, wherein the second reactant includes a color indicator, an oxidant and a metal salt mixture.

4. The apparatus for residual pesticide detection as claimed in claim 1, wherein the first reactant is preformed on the first strip portion, and the second reactant is preformed on the second strip portion.

5. The apparatus for residual pesticide detection as claimed in claim 1, wherein the mixing container is for containing the mixed aqueous solution formed by the sample liquid to be tested and the second reactant.

6. The apparatus for residual pesticide detection as claimed in claim 5, wherein the mixing container is further provided with an ultraviolet light for irradiating the sample liquid to be tested, and the mixing container is a reusable reused mixing container.

7. The apparatus for residual pesticide detection as claimed in claim 1, wherein the disposable electrode strip is further provided with a cover layer having a partial gas vent that is arranged over the working electrode area.

8. The apparatus for residual pesticide detection as claimed in claim 1, wherein detection of target pesticide normality in the sample liquid to be tested performed by the electrical signal analyzer is processed by taking degrees of current signal generated by the electrical signal analyzer in connection to different concentration of the target pesticide so as to obtain the target pesticide normality in relation to the corresponding normality of predetermined pesticide by referring to a calibration curve of the predetermined pesticide that is obtained by degrees of current signal generated by the electrical signal analyzer in connection to different concentration of the predetermined pesticide.

9. The apparatus for residual pesticide detection as claimed in claim 8, wherein the target pesticide normality is selectively expressed in unit of ppm, ppb, ppt, mg/L, mmol/dL or mg/dL, and the calibration curve used for obtaining the target pesticide normality is different for each of the different types of the predetermined pesticides.

10. The apparatus for residual pesticide detection as claimed in claim 9, wherein the different types of the predetermined pesticides used for obtaining the calibration curves organophosphate pesticide, carbamate pesticide and neonicotinoid pesticide.

* * * * *